United States Patent [19]

Coffman et al.

[11] Patent Number: 4,656,026
[45] Date of Patent: Apr. 7, 1987

[54] MAGNETIC RESONANCE (MR) IMAGE ENHANCEMENT COMPOUNDS FOR SPECIFIC AREAS OF THE BRAIN

[75] Inventors: Jeffrey A. Coffman; Charles F. Barfknecht, both of Iowa City, Iowa

[73] Assignee: University of Iowa Research Foundation, Iowa City, Iowa

[21] Appl. No.: 680,058

[22] Filed: Dec. 10, 1984

[51] Int. Cl.$^4$ .................. A61K 49/00; A61B 5/05; A61B 6/00
[52] U.S. Cl. .................. 424/9; 128/653; 128/654; 436/173; 436/803; 436/806; 540/512; 540/514
[58] Field of Search .................. 128/653, 654; 424/9; 436/173, 803, 806; 540/512, 514

[56] References Cited

U.S. PATENT DOCUMENTS

| | | |
|---|---|---|
| 3,789,832 | 2/1974 | Damadian . |
| 3,932,805 | 1/1976 | Abe et al. . |
| 4,016,146 | 4/1977 | Soares .................. 436/803 |
| 4,240,439 | 12/1980 | Abe et al. . |
| 4,254,778 | 3/1981 | Clow et al. . |
| 4,315,216 | 2/1982 | Clow et al. . |
| 4,449,097 | 5/1984 | Young et al. . |

OTHER PUBLICATIONS

Keana, J. F., Chemical Reviews, vol. 78, (1978), pp. 37-64.
Brasch, Robert C., "Work in Progress: Nuclear Magnetic Resonance Study of a Paramagnetic Nitroxide Contrast Agent for Enhancement of Renal Structures in Experimental Animals", Radiology 147, 773 (1983).
Brasch, Robert C., "Brain Nuclear Magnetic Resonance Imaging Enhanced by a Paramagnetic Nitroxide Contrast Agent: Preliminary Report" AJR 141, 1019 (1983).
Brasch, Robert C., "Nuclear Magnetic Resonance Session" Investigative Radiology Jul.-Aug., 1984 (S148).

Primary Examiner—Christine M. Nucker
Assistant Examiner—Stephen C. Wieder
Attorney, Agent, or Firm—Zarley, McKee, Thomte, Voorhees & Sease

[57] ABSTRACT

An improved imaging technique involving nuclear magnetic resonance. Known drug or neurotransmitter receptor ligands are covalently bound to magnetic resonance image enhancing spin label compounds, such as sterically hindered free radical nitroxide compounds, with the resulting adduct being administered to a patient, and thereafter when the ligand is bound to specific receptor sites in the soft tissue such as the brain, regional tissue area is assessed with nuclear magnetic resonance, allowing diagnostic discrimination.

14 Claims, No Drawings

MAGNETIC RESONANCE (MR) IMAGE ENHANCEMENT COMPOUNDS FOR SPECIFIC AREAS OF THE BRAIN

BACKGROUND OF THE INVENTION

The ability to assess the living brain in vivo has developed only recently. Beginning with electroencephalography pneumoencephalography and nitrous oxide cerebral blood flow studies from the 1930's to the 1960's evaluative methods remained crude. However, numerous abnormalities, albeit none of them specific, were discovered in the psychiatrically ill, particularly among schizophrenics. In the latter portion of the 1970's, the advent of computed tomography (CT) offered a much enhanced perspective of brain structure. The application of CT to psychiatric patient populations led to extension and confirmation of pneumoencephalographic data regarding ventricular enlargement.

However, the information afforded by CT centers primarily on gross structural changes and although some information can be extracted comparing regional tissue structure, brain function (physiologic, pharmacologic or biochemical) is not illuminated. A direct result of the data processing techniques developed for CT is that a number of new and powerful imaging methods have lately been introduced, specifically positron emission tomography (PET) and magnetic resonance (MR) imaging. These two techniques are particularly hopeful as the physical properties upon which imaging data derive allow for measurement of many biochemical parameters not accessible by computed tomography. PET depends on the processing of data generated by an array of gamma ray detectors surrounding the subject under study. The technique then allows for in vivo tissue localization of gamma ray emitting or positron emitting (secondarily generating gamma radiation) radionuclides. When these radionuclides, such as $^{11}C$, $^{15}O$, $^{18}F$, are joined to biological compounds of interest, a topographical map of tissue distribution can be generated. This has been demonstrated for glucose metabolism and pharmaceutical binding sites such as dopamine and benzodiazepine receptors.

In spite of the tremendous potential of PET as a tool for assessing various receptor sites in vivo, certain significant limitations remain. These center primarily upon the radio-label which is required. Positron emitting radionuclides have generally brief half lives and are therefore subject to rapid decay. This fact imposes a number of restrictions on PET related research such as the need for a cyclotron facility as a source of radionuclides must be located nearby. Also, a nuclear chemist and nuclear pharmacist with access to appropriate substance handling facilities must be available for synthesis, purification, and preparation of the desired compound. Both of these factors create significant degrees of expense. The subject must be kept immediately available for administration of the study compound and the researcher must be willing to accept the risk of exposing experimental subjects to ionizing radiation. This last point precludes examination of normal populations of significant size or repeated study designs.

In addition to offering the disadvantage of exposing the patient to ionizing radiation, PET also will not produce a very clear image, since the noise-to-signal ratio is quite high. Put another way, the primary determination of the quality of image in PET is the radiation dose one can administer. Thus, in order to obtain clearer images, one needs a larger radiation dose. However, there is of course a maximum safe limit which the patient can withstand. Thus, image clarity must be sacrificed for patient safety.

Nuclear magnetic resonance, now commonly referred to as magnetic resonance (MR) represents an imaging technique which, although it relies on similar methods of image reconstruction to those applied in CT and PET, utilizes an entirely new source of data for image processing, specifically the energy released by certain nuclei when they resonate, i.e. are promoted to, and then decay from a higher energy state, due to radio frequency (RF) electromagnetic radiation within a strong magnetic field. A number of nuclei, for example, $^1H$, $^{13}C$, $^{14}N$, $^{19}F$, $^{31}P$, possess the property, nonzero spin, necessary to produce a magnetic resonance signal. Fortunately, hydrogen is the most common nucleus in tissue, therefore making an image of relative populations of protons possible. As the MR signal intensity is changed by alterations in the local physical and chemical environment, sufficient variability in the processed image is present to distinguish various tissue types. This can be done through plots of relative signal strength or through plots of the time period required for emission of the radio signal following excitation. Several properties of MR allow for the development of tissue specific markers which could potentially be mapped on the MR image.

One property of MR which is altered under a variety of conditions is that of relaxation time, values describing that period required for excited nuclei to return to their resting state. Depending on the sequence of exciting RF pulses, two different relaxation times, $T_1$ and $T_2$, can be measured. A number of chemical environmental factors affect these relaxation times. Proton relaxation enhancement can be produced by local increases in paramagnetic substances which have unbalanced electron spins. The presence of the paramagnetic compounds produces local decreases in $T_1$ and increases in $T_2$ while generally enhancing overall image intensity. A number of such substances are currently under study by radiological investigators for use as potential intravascular contrast agents, see Brasch et al. Radiology, 147, 773 (1983). These include a number of metals ions of the transition series such as $Mn^{+2}$, $Mn^{+3}$, $Fe^{+2}$, $Fe^{+3}$ and of the lanthanide series such as $Gd^{+3}$. These are useful when chelated by EDTA or an hematoporphyrin complex. However, the necessity of chelation appears to limit these agents to use largely as intravascular agents. These intravascular contrast agents are not suitable for soft tissue studies of localized sites, such as in the brain since the agents themselves are often toxic they will not localize when bound to EDTA, and thus cannot be used for such purposes.

Accordingly, it is a primary objective of the present invention to develop a new method of MR image enhancement to allow specific marking, evaluation and study of localized areas of soft tissues, such as the brain.

Another objective of the present invention is to provide an image enhancement technique which does not employ ionizing radiation, at all.

A further objective of the present invention is to provide an image enhancement technique for regionally mapping soft tissue and which provides clear magnetic resonance images.

A even further objective of the present invention is to provide diagnostic techniques for regionally mapping soft tissues by magnetic resonance which employ psychoactive drugs bound to spin label compounds, such as nitroxide stable free radicals.

A yet further objective of the present invention is to provide improved tissue study techniques which employ sterically hindered stable free nitroxide radicals covalently bound to psychoactive drugs.

A further objective of the present invention is to provide certain compounds which are structurally modified psychoactive drugs having covalently bound thereto sterically hindered free nitroxide radical.

A still further objective of the present invention is to provide an improved diagnostic tool which will allow diagnostic development of more information, both for treatment and continuing research, for mental disorders such as schizophrenia, mania, depression, dementia, anxiety neurosis, or movement disorders such as Parkinson's Disease, Huntington's Disease, and for seizure disorders including generalized and localized, and partial seizures as well as complex seizures.

The method and manner of accomplishing each of the above objectives, as well as others, will become apparent from the detailed description of the invention which follows hereinafter.

DETAILED DESCRIPTION OF THE INVENTION

This invention, inter alia relates to synthesis and evaluation of new compounds for marking specific areas of soft tissues such as the brain. The compounds represent valuable diagnostic tools, since currently there are no such reagents available for use with nuclear magnetic resonance imaging techniques.

Certain compounds of low toxicity have been discovered to bind to specific molecular recognition sites (drug receptor or neurotransmitter receptor sites) within tissue. The primary area in which these discoveries have occurred has been the brain due to the high population and diversity of such sites within nervous tissue although such sites are present throughout the body. Awareness of receptor sites in the body has emerged from pharmacological studies originally intended to discover the bases of action for drugs empirically found to be useful in the treatment of various disorders. It is believed that many disorders, particularly those of the nervous system, are due to altered activity in various receptor populations. Through study of the regional distribution and activity of these varied receptor systems a picture of tissue function can be derived. The initial step in any such study involves the selection of compounds which will selectively interact with the sites of interest.

One very important neurotransmitter/drug receptor system in the brain and an example to be considered in detail is the gamma-aminobutyric acid (GABA) - benzodiazepine chloride ionophore system. In these receptor-ionophore complexes binding of one ligand to its receptor site enhances binding of the other site's ligand and both tend to enhance the activity of the ionophore in reducing neuronal excitation. A variety of ligand compounds, including some widely used drugs, the benzodiazepines, bind to one or the other of these sites. As far as is known, the antianxiety and anticonvulsant action of the benzodiazepine class of drugs as well as the sedative and anticonvulsant activity of GABAergic drugs (those drugs directly enhancing GABA action) is due to their action on their common receptor complex. Therefore, there are two approaches providing access to the study of this complex. One is to utilize a benzodiazepine such as diazepam (Valium), chlordiazepoxide (Librium), oxazepam, clonazepam, or flunitrazepam for a site recognition ligand. Alternatively one could make use of a GABA receptor site ligand such as baclofen or muscimol.

Another neurotransmitter-receptor system of interest is the dopaminergic system. The relationship of the activity of this system to psychopathological symptoms is not entirely clear, however, its importance is inferred through the effectiveness of dopamine receptor antagonists in abating psychotic symptoms. A number of compounds of different classes have this desired effect and would lend themselves to adaptation for study of their sites of activity. These would include drugs of the butyrophenone class such as spiperone, haloperidol (Haldol) and droperidol; drugs of the phenothiazine class such as trifluoperazine and thiothixene; and drugs of the benzamide class such as sulpiride. Alternatively, dopamine receptor agonists, such as bromocriptine, might serve as useful ligand substrates for study of the dopaminergic system, particularly among individuals suffering from parkinsonism.

Still another class of compounds with receptor activity and clinical importance are antidepressants most commonly tricyclic antidepressants. Ligand substrates for these receptors could be derived from imipramine, amitriptyline, bupropion and nomifensene.

Other receptor systems of interest for which ligand substrates could be created and which may have a bearing on gaining understanding of a variety of disorders exist. These include adrenergic receptors, serotonergic receptors, histamine receptors, excitatory amino acid receptors, opiate receptors, peptidergic receptors, and cholinergic receptors.

Given access to desired receptor sites through site specific ligand compounds, it becomes important to address the manner in which the site localization of these molecules can be assessed. As has been noted earlier, techniques exist at present for radioactive labeling of such site selective ligands, however, the purpose of the present invention is to mark similar receptor site ligands with "MR visible" labels.

The term "ligand" has been used herein to generally describe the tissue binding portion of the active molecules referred to above. It can be seen that for the most part the molecules are psychoactive drugs. However from time to time the broader term "ligand" is used because many of the useful compounds may well be derived from psychoactive drugs, but they themselves may not be the active drug form.

Generally, the MR enhancing imaging reagents of this invention consist of three portions, or moieties in the molecule. The first is a selective ligand often referred to herein as a psychoactive drug, generally described above, which is known to bind to specific sites; the second is a small connecting chain attached at a non-interfering portion of the psychoactive drug and containing functionality which will allow covalent attachment to the third portion; and the third portion is a spin label enhancer, which must have functionality that can form a covalent bond with the connecting chain.

In accordance with this invention, the spin label enhancers for covalent bonding to the psychoactive drug are stable, sterically hindered, free radical compounds. Generally speaking, the most preferred of these are nitroxides.

Free radicals are ordinarily molecules, rather than single ions, which have one or more unpaired electrons in molecular orbital making them paramagnetic, and also highly reactive. When the unpaired electron can be sterically hindered preventing the pairing of the electron with another molecule the free radical becomes relatively nonreactive. A number of these compounds have been synthesized. Of particular note are nitroxide-stable free radicals (major subgroups including piperidine and pyrrolidine derivatives) which can be bonded covalently to other molecules. These compounds make ideal MR contrast agents. They are stable and essentially nonreactive over a wide temperature (to 123° C.) and pH (1.7 to 10) range. They strongly enhance proton relaxation and they have a potential for chemical bonding which allows labeling of target specific biomolecules. In this invention practical but tissue specific markers have been developed which represent a covalent binding of a free radical nitroxide to a psychoactive drug.

Stable sterically hindered free radical nitroxides are known compounds, see for example Keana, "Newer Aspects of Synthesis and Chemistry of Nitroxide Spin Labels", *Chemical Reviews*, 1978, Vol. 78 No. 1, pp. 37–64, which disclosure is incorporated herein by reference. Since the Keana article is fairly exhaustive with regard to description of suitable nitroxide spin labels which may be used in this invention, there is no need to repeat in detail the disclosure thereof. However, generally, basic building blocks of the nitroxide suitable for this invention are those derived from 2,2,6,6-tetramethylpiperidine-N-oxyl (often referred to a TEMPO), 2,2,5,5-tetramethylpyrroline-N-oxyl, and 4,4-dimethyloxazolidine-N-oxyl which is a doxyl nitroxide. All of these compounds are paramagnetic and hence capable of excitation or changes in magnetic resonance energy levels and therefore provide clearer imaging. One may use generally doxyl nitroxides, proxyl nitroxides, azethoxyl nitroxides, imidazoline derived nitroxides, tetrahydrooxazine derived nitroxides, and the recently synthesized steroid nitroxides, etc. Of course, the most common method of covalent attachment of a nitroxide spin label compound to another molecule is by way of a substitution reaction on the nitroxide molecule, for example, nitroxide alkylating agents or acylating agents.

It should be mentioned that spin labeling, as the term is used herein, is understood to mean "spin label" as that is defined in the Keana article, namely when a nitroxide bearing molecule is covalently attached to another molecule of interest and the nitroxide grouping does not significantly disturb the behavior of the spin label molecule in the system under study. Thus, the nitroxide molecule being paramagnetic, simply enhances the energy or excitation level subjected to the magnetic field during the magnetic resonance.

In the studies of this investigation, the most preferred spin label free radical nitroxide compounds are TEMPO, 2,2,5,5-tetramethylpyrroline-N-oxyl and 4,4-dimethyloxazolidine-N-oxyl.

The reaction between the nitroxide and the desired receptor site ligand such as a pyschoactive drug is a simple straightforward reaction. Before discussing this reaction it should perhaps be mentioned that both the psychoactive drugs and the nitroxide compounds are currently commercially available. Psychoactive drugs are, or course, available from any pharmaceutical house and the nitroxides, such as TEMPO can be purchased through Sigma Chemical Company of St. Louis, Missouri or Aldrich Chemical Company of Milwaukee, Wisconsin.

As will be apparent in the examples below, the reaction between nitroxide free radical and the psychoactive drug is a simple straightforward addition reaction and can generally be represented as acylation or alkylation. To date, the satisfactory covalently linked nitroxides and psychoactive drugs prepared include 1-(2-aminoethyl-4-isocyano-2,2,6,6,-tetramethylpiperidine-N-oxyl nordiazepam, phenylethylamino-2,2,6,6-tetramethylpiperidine-N-oxyl-thiourea and a clonazepam analog, the structure of which is detailed in the examples below. To date, as will be apparent from the examples below, all testing of these drugs has been in vitro testing.

The following examples are offered to illustrate but not limit the product and process of this invention.

EXAMPLES

In particular, phenylethylamino-2,2,6,6-tetramethyl-piperidine-N-oxyl-thiourea (herein after abbreviated PEATT) was prepared. It represents TEMPO attached to phenylethylamine, a known psychoactive compound. Rats administered the spin labeled phenylethylamine were observed to have their stereo-typical, altered behavior pattern. When the rats were administered spin label PEATT they likewise were observed to have the stereotypical phenylethylamine altered behavior pattern. This indicates that the spin label nitroxide had no effect upon the drug functionality. A magnetic resonance pattern of methanol was selected as a standard. The PEATT was dissolved in the methanol at various concentrations, both $T_1$ and $T_2$ were measured. It can be seen from the table below that comparing the data from each that the spin label nitroxide significantly shortened relaxation times, indicating that image enhancement would occur in vivo. Thus, both tests confirm that soft tissue image enhancement magnetic resonance techniques can be successfully accomplished.

Synthetic Procedures:
1. Synthesis of PEATT, 2-phenylethylamine TEMPO thiourea.

To a solution of 1.205 g. [5.7 mmole]of 4-isothiocyanato-TEMPO in 15 ml. of anhydrous diethyl ether was added 0.86 g. [7.1 mmole]of PEA, 2-phenylethylamine, in 10 ml. of diethyl ether. After 24 hours of stirring at room temperature, the precipitated product was allowed to settle and the ether removed. After washing three times with petroleum ether [20 ml. portions], the product was dried in vacuo to yield 1.67 g. [5.0 mmole]of PEATT. Yield 88%. Purification was accomplished on a flash column, using silica gel as the adsorbent and methylene chloride:hexane:methanol [14:6:1]was the solvent.

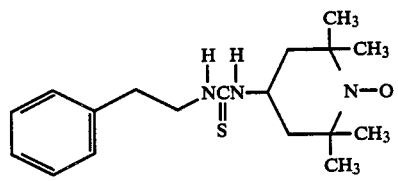

2. Synthesis of 1-[2-aminoethyl]-nordazepam TEMPO thiourea.

There are several steps from the readily available starting material, chlordiazepoxide, to the spin label product. One step is a repetition of the common literature preparation of nordazepam, which one follows for a very closely related analog [preparation of 1-[2-aminoethyl]nordazepam], and the third is the reaction of an amine with an isothiocyanate to form a thiourea.

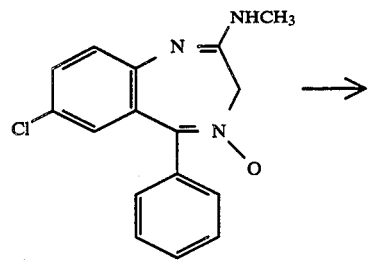

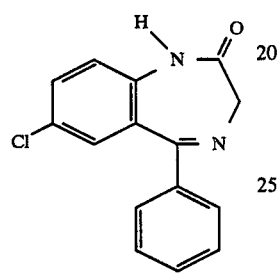

a. Preparation of Nordazepam from chlordiazepoxide.

Literature Reference: L. H. Sternbach and E. Reeder, Journal of Organic Chemistry, Volume 26, pp. 4936-4941 [1961], entitled, "Quinazolines and 1,4-Benzodiazepines. IV. Transformations of 7-chloro-2-methylamino-5-phenyl-3H-1,4-benzodiazepine-4-oxide." This procedure was followed and is incorporated by reference.

b. Preparation of 1-[2-aminoethyl]nordazepam from nordazepam.

Literature Reference: J. V. Earley, R. I. Fryer, D. Winner, and L.H. Sternbach, Journal of Medicinal Chemistry, Volume 11, pp. 774–777 [1968], entitled, "Quinazolines and 1,4-Benzodiazepines. XL."

In this literature reference they synthesized 1-[2-aminoethyl]-5-[2-fluorophenyl]-7-chloro-1,3-dihydro-2H-1,4-benzodi azepine-2-one which differs from the present compound only by the 2-fluoro group in the 5-phenyl substituent. The procedure however was the same and is incorporated by reference.

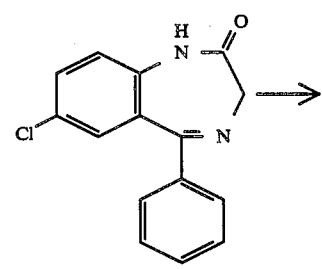

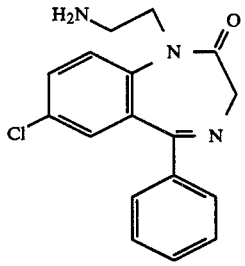

c. Preparation of 1-[2-aminoethyl]-nordazepam TEMPO thiourea.

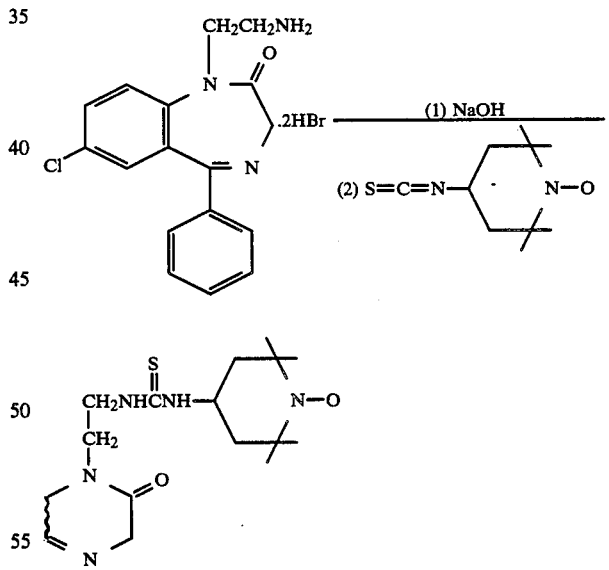

This compound was prepared as follows.

1-(2-Aminoethyl)-nordazepam dihydrobromide (69.0 mg; 0.146 mmol) was dissolved in $H_2O$ (1.0 mL). To the aqueous solution was added 4N NaOH (4 mL) and the resulting suspension was extracted with three portions (20 mL) of ether. The ether extracts were combined, dried over $Na_2SO_4$, and evaporated to give the free base of nordazepam as an oil. The oil was dissolved in ether (15 mL) and stirred at room temperature while TEMPO isothiocyanate (43.4 mg; 0.186 mmol) was added. The reaction was stirred overnight, the ether removed under reduced pressure, and the resulting residue chromatographed (9×200 mm column) on Davisil 633 silica gel (Aldrich Chem. Co.) with EtOAc. The second material to be eluted from the column was collected and the solvent evaporated to give the spin-labelled product (48.65 mg; 0.93 mmol) in a 63.5% yield. The structure was confirmed by chemical ionization mass spectrometric analysis showing the appropriate molecular ion and fragmentation pattern.

3. Preparation of 1-[acetamidomethyl-PROXYL]-Clonazepam.

This compound has the formula:

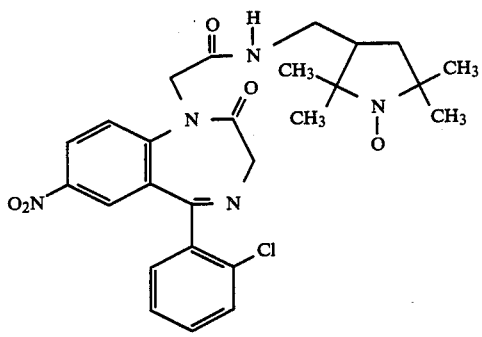

It was prepared as follows:

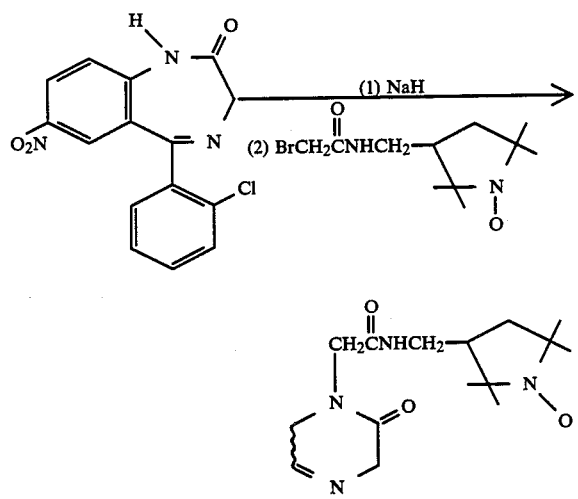

Clonazepam (50.8 mg; 0.16 mmol) was dissolved in dry DMF (3.0 mL) and cooled to 0° under $N_2$. Sodium hydride, 60% in mineral oil, (10.0 mg; 0.25 mmol) was added at 0° turning the reaction a bright yellow. The reaction was stirred at room temperature for 1 hour, then cooled to 0°. 3-(2-Bromoacetamidomethyl)-PROXYL (50.0 mg; 0.17 mmol) in DMF (1.0 mL) was added in two equal portions over a 10 minute period. The reaction, which turned a dark red, was stirred overnight at room temperature, then evaporated under vacuum to give a dark residue. The residue was chromatographed (9×200 mm column) on Davisil 633 silica gel (Aldrich Chem. Co.) with EtOAc/pet ether (4:1). The product, which was the second material to be eluted from the column, was obtained in a 75.5% yield (63.5 mg; 0.12 mmol). The structure was confirmed by chemical ionization mass spectrometric analysis, showing the appropriate molecular ion and fragmentation pattern.

Comparable Behavioral Effect of β-Phenylethylamine-HCL and PEATT Phenylethylamino-TEMPO-thiourea)

Following the method of Braestrup and Randrup (1978), Braestrup, C. and Randrup, A., pp. 248–250 in Mosnaim, A. and Wolf, M. (eds.) Noncatecholic Phenylethylamines: Part 1, Phenylethylamine: Biological Mechanisms and Clinical Aspects. Marcel Dekker Inc., New York, 1978, which is incorporated herein by reference, the relative behavioral effect of phenylethylamine and its TEMPO-labeled cogener, phenylethylamine-TEMPO-thiourea (PEATT) was made. The above authors have reported that a dose of 80 mg per kilogram of phenylethylamine (PEA) administered intraperitoneally in rats results in a short-lasting stimulation with high intensity. Ten minutes after injection rats assume a crouched posture and perform continuous sniffing for approximately 35 minutes. This behavior is similar to that induced to D-amphetamine with the exception that the sniffing behavior occurs alone without any locomotion or rearing.

A side by side comparison study was undertaken. Three male Sprague-Dawley rats, each weighing approximately 250 mg were selected for study. The rats were weighed individually to allow for dosage calculation. Rat #1 was given an intraperitoneal injection of 1 cc of propylene glycol vehicle. Rat #2 was given a dose of 80 mg per kilogram phenylethylamine hydrochloride in propylene glycol vehicle, and rat #3 was given again intra-peritoneally an 80 mg per kilogram dose of PEATT in 1 cc propylene glycol. Rat #1 when returned to its cage showed a brief reduction in normal exploratory activity lasting nearly two minutes whereupon exploration occurred once again. Rats #2 and 3 again showed a two minute reduction in the normal exploratory behavior which again resumed until approximately 10 minutes after injection. At this point both rats #2 and 3 assumed a crouched posture and exhibited a side to side sniffing motion. This behavior continued until about 45 minutes following injection for rat #2 and approximately 60 minutes following injection for rat #3. In addition, rat #3 when compared to rat #2 appeared to exhibit greater persistence of the stereotypic behavior then rat #2. This was noted in that disturbance of the cage briefly caused a slight reduction in the stereotypy observed in rat #2 while this was not the case in rat #3.

These preliminary findings indicate that the behavioral effects of PEATT are similar to those induced by PEA, the unlabeled drug. In addition, perhaps due to greater lipid solubility the effect of PEATT appear to be greater in its persistence than that observed with the unlabeled PEA. This occurred in spite of the fact that the dose of PEATT administered was not equivalent in lower quantity to the dose of PEA administered. The labeling of PEA with the tempo thiourea substituent does not result in a reduction in its pharmacologic activity.

Effect of PEATT on Methanol's Proton MR Relaxation Constants

Method:

PEATT (phenylethylamino-TEMPO-thiourea) was dissolved in varying concentrations in spectroscopic grade methanol. Measurement of $T_1$'s was accomplished by the inversionrecovery technique while $T_2$'s were measured by spin-echo. All measurements were performed on a 360 MHz technical MR spectroscope at 25° C. Values are given separately for the hydroxyl and methyl protons.

| TABLE of Methanol $T_1$ and $T_2$ Data | | | |
|---|---|---|---|
| PEAT Concentration | Methanol Proton | $T_1$* (sec) | $T_2$* (sec) |
| 0 | CH$_3$ | 4.51 | 0.65 |
|  | OH | 4.05 | 0.24 |
| 0.1 mM | CH$_3$ | 4.32 | 0.58 |
|  | OH | 3.90 | 0.22 |
| 0.25 mM | CH$^3$ | 4.21 | 0.42 |
|  | OH | 3.35 | 0.17 |
| 1.0 mM | CH$_3$ | 3.50 | 0.33 |
|  | OH | 1.88 | 0.14 |
| 5.0 mM | CH$_3$ | 1.95 | 0.29 |
|  | OH | 0.66 | 0.10 |

*$T_1$ refers to the spin-lattice relaxation time and characterizes the rate that the Z-component of the magnetization returns to its equilibrium value. This rate is enhanced when molecular motion sets up fluctuating local fields. $T_2$ refers to the spin-spin relaxation time and characterizes the rate of decay of the magnetization in the x-y plane. Both $T_1$ and $T_2$ are well known terms to those familiar with MR spectroscopy.

What is claimed is:

1. A method of soft tissue imaging especially adapted for localized tissue areas such as brain tissue receptor sites, comprising:
    administering to a patient a spin label image enhancer covalently bonded to a non-toxic ligand which is known to bind to certain regionally specific drug receptor sites; and thereafter,
    obtaining measurements of the resulting magnetic resonance signal and assessing signal alterations to thereby diagnose the regional tissue area;
    said ligand being selected from the group consisting of agonists and antagonists of benzodiazepine receptors, GABA receptors, dopamine receptors, adrenergic receptors, serotonergic receptors, histaminic receptors, excitatory amino acid receptors, opiate receptors, peptidergic receptors, cholinergic receptors;
    said spin label enhancer being a compound which will covalently bond to said ligand and which will at the same time retain its spin label functionally without interferring with the legand's regional functionality.

2. The method of assessing mental conditions, movement disorders, and seizure disorders, with potential for diagnostic discrimination, comprising:
    administering to a patient who is to be assessed a nitrogen bonded nitroxide-drug compound; and thereafter,
    magnetic resonance measuring of the tissue to determine localization of said bonded nitroxide-drug compound followed by evaluating the regional distribution as an assessment of mental conditions, movement disorders, and seizure disorders;
    said bonded nitroxide-drug compound being bonded to a non-toxic ligand known to bind to certain regional specific drug or neurotransmitter receptor cites when administered to patients, and itself having been reacted with a sterically hindered free radical nitroxide to form a covalent bond between said nitroxide and said ligand.

3. The method of claims 1 or 2 wherein said ligand is a benzodiazepine.

4. The method of claims 1 or 2 wherein said ligand is a dopamine antagonist, antipsychotic drug.

5. The method of claim 4 wherein the dopamine antagonist is derived from SPIPERONE.

6. The method of claims 1 or 2 wherein said ligand is a tricyclic antidepressant.

7. The method of claim 6 wherein said antidepressant is derived from imipramine.

8. The method of claims 1 or 2 wherein said magnetic resonance enhancing spin label compound is a stable, sterically hindered free radical.

9. The method of claim 8 wherein the sterically hindered free radical compound is a nitroxide.

10. The method of claim 8 wherein said nitroxide is a derivative of a stable free radical compound selected from the group consisting of 2,2,6,6-tetramethylpiperidine-N-oxyl (TEMPO), 2,2,5,5-tetramethylpyrroline-N-oxyl, and 4,4-dimethyloxazolidine-N-oxyl.

11. The method of claim 10 wherein the nitroxide is TEMPO.

12. 1-(2-aminoethyl-4-isocyano-2,2,6,6-tetramethyl-piperidine-N-oxyl) nordiazepam.

13. Phenylethylamino-2,2,6,6,tetramethylpiperidine-N-oxyl-thiourea.

14. 1-]Acetamidomethyl-3-(2,2,5,5-tetramethyl-pyrrolidinyl-1-oxide)]-clonazepam.

* * * * *